United States Patent [19]

Vora et al.

[11] Patent Number: 4,806,695

[45] Date of Patent: Feb. 21, 1989

[54] PROCESS FOR ETHERIFICATION OF A DEHYDROGENATION ZONE EFFLUENT

[75] Inventors: Bipin V. Vora, Darien; Norman H. Scott, Arlington Heights, both of Ill.

[73] Assignee: UOP Inc., Des Plaines, Ill.

[21] Appl. No.: 114,965

[22] Filed: Oct. 30, 1987

[51] Int. Cl.$^4$ .............................................. L07C 41/06
[52] U.S. Cl. .................................................... 568/697
[58] Field of Search ........................................ 568/697

[56] References Cited

U.S. PATENT DOCUMENTS

| | | | |
|---|---|---|---|
| 2,720,547 | 10/1955 | Wolff et al. | 260/614 |
| 4,118,425 | 10/1978 | Herbstman | 260/614 A |
| 4,219,678 | 8/1980 | Obenaus et al. | 568/697 |
| 4,329,516 | 5/1982 | Al-Muddarris | 568/697 |
| 4,465,870 | 8/1984 | Herskovits | 568/697 |

OTHER PUBLICATIONS

Chemical Engineering News, Jun. 25, 1979 Edition, p. 35.
Huls-Process; Methyl Tertiary Butylether, presented at the American Institute of Chemical Engineers, 85th National Meeting on 6-4-78, by F. Obenaus et al.
Hydrocarbon Processing, Oct. 1980 Edition, p. 91.

*Primary Examiner*—Howard T. Mars
*Attorney, Agent, or Firm*—Thomas K. McBride; John G. Tolomei

[57] ABSTRACT

A combined process for the dehydrogenation of $C_3$–$C_5$ paraffins in a first zone and the conversion of olefins in a second zone improves efficiency by directly charging all but the lightest components of the dehydrogenation zone effluent to the olefin conversion zone. This process is particularly suited for the production of gasoline boiling range ethers where an isoparaffin is dehydrogenated in a first zone to produce isoolefins. After separation of hydrogen and methane, the dehydrogenation zone effluent is charged along with a $C_1$–$C_5$ alcohol to an etherification zone for the production of ether. The etherification zone effluent is separated into at least two component streams one comprising light ends, isoparaffins, and oxygenates and the other comprising an ether product. After passage through an alcohol recovery zone, the isoparaffins are separated from the other lighter recycled material and combined with the feed to dehydrogenation zone. A particular arrangement of this invention uses an etherification zone for the production of MTBE and two fractionation columns to yield an overhead stream of light ends, a stream of recycle isoparaffins and methanol, and a product stream of MTBE. The arrangement also simplifies the recovery of oxygen containing compounds by allowing the use of only a methanol recovery zone without the additional cost of a separate oxygenate recovery unit.

13 Claims, 1 Drawing Sheet

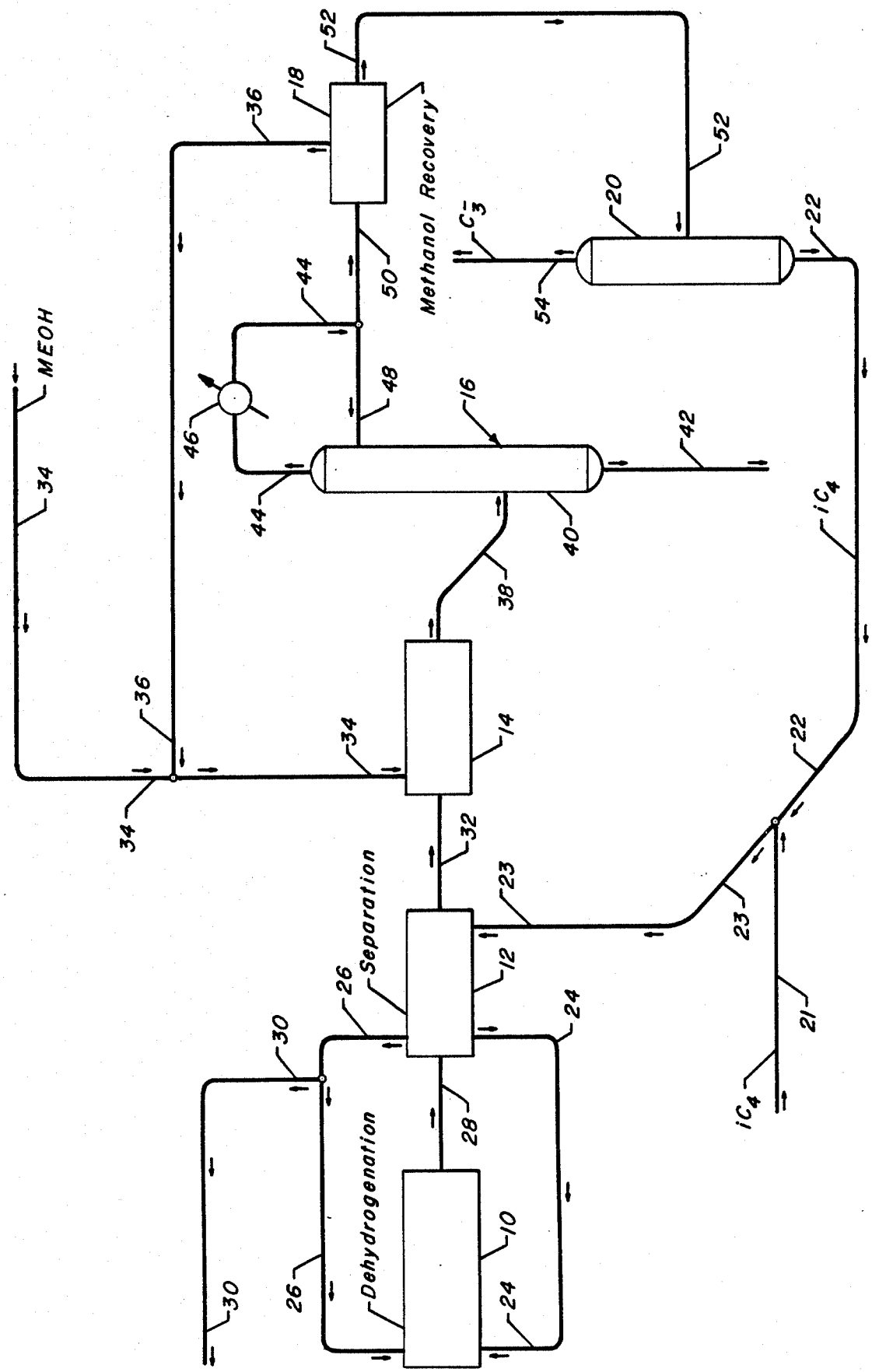

4,806,695

PROCESS FOR ETHERIFICATION OF A DEHYDROGENATION ZONE EFFLUENT

FIELD OF THE INVENTION

This invention relates broadly to processes for the production of ethers by the reaction of olefins. The invention more directly relates to processes for the etherification of a dehydrogenation effluent and the recycle of dehydrogenatable materials from the etherification zone to the dehydrogenation zone.

BACKGROUND OF THE INVENTION

Processes for producing olefins by the dehydrogenation of saturated hydrocarbons are well known. A typical dehydrogenation process mixes the feed hydrocarbons with hydrogen and heats the resulting admixture by indirect heat exchange with the effluent from the dehydrogenation zone. Following heating, the feed mixture passes through a heater to further increase the temperature of the feed components before it enters the dehydrogenation zone where it is contacted with the dehydrogenation catalyst. The catalyst zone may be operated with a fixed bed, a fluidized bed, or a movable bed of catalyst particles. After heat exchange with the feed, the dehydrogenation zone effluent passes to product separation facilities. The product separation facilities will typically produce a gas stream, made up primarily of hydrogen, a first product stream that includes the desired olefin products, and a second potential product stream comprising light hydrocarbons. The light hydrocarbon stream typically has fewer carbon atoms per molecule than the desired olefin product. Light hydrocarbons are generally removed from the product stream in order to reduce flow volume, operating pressures, and undesirable side reactions in downstream process units that receive the olefin product. A portion of the hydrogen stream is typically recycled to the dehydrogenation zone to provide hydrogen for the combined feed stream. The product stream usually contains unconverted dehydrogenatable feed hydrocarbons in addition to the product olefin. These unconverted hydrocarbons may be withdrawn in the separation facilities for recycle to the dehydrogenation zone or passed together with the product olefins to an etherification zone for conversion of the product olefins to ethers. Etherification processes are currently in great demands for making high octane compounds which are used as blending components in lead-free gasoline. These etherification processes will usually produce ethers by combination of an isoolefin with a monohydroxy alcohol. The etherification process can also be used as a means to produce pure isoolefins by cracking of the product ether. For instance, pure isobutylene can be obtained for the manufacture of polyisobutylenes and tert-butylphenol by cracking methyl tertiary butyl ether (MTBE). The production of MTBE has emerged as a predominant etherification process which uses $C_4$ isoolefins as the feedstock. A detailed description of processes, including catalyst, processing conditions, and product recovery, for the production of MTBE from isobutylene and methanol are provided in U.S. Pat. Nos. 2,720,547 and 4,219,678 and in an article at page 35 of the June 25, 1979 edition of Chemical and Engineering News. The preferred process is described in a paper presented at The American Institute of Chemical Engineers, 85th National Meeting on June 4–8, 1978, by F. Obenaus et al. Another etherification process of current interest is the production of tertiary amyl ether (TAME) by reacting $C_5$ isoolefins with methanol.

Due to the limited availability of olefins for etherification, it has become common practice to produce them by the dehydrogenation of isoparaffins and to pass the dehydrogenation effluent to an etherification process. General representations of flow schemes where a dehydrogenation zone effluent passes to an etherification zone are shown in U.S. Pat. Nos. 4,118,425 and 4,465,870. More complete representations of a flow arrangement where the dehydrogenation zone effluent passes to an etherification zone are given in U.S. Pat. No. 4,329,516 and at page 91 of the October, 1980 edition of Hydrocarbon Processing. The latter two references depict the typical gas compressin and separation steps that are used to remove hydrogen and light ends from the dehydrogenation zone effluent before it passes to the etherification zone. A typical effluent from an etherification zone includes an ether product, unreacted alcohol, and unreacted hydrocarbon. These effluent components enter separation facilities that yield the ether product, alcohol for recycling to the etherification zone, hydrocarbons for further processing into dehydrogenation. This recycle stream of $C_4$ or $C_5$ isoparaffins, prior to recycling to the dehydrogenation zone, is usually treated to recover methanol and remove other oxygenates which are harmful to the dehydrogenation catalyst.

As evidenced by the foregoing references, the light materials that are present with the effluent from the dehydrogenation zone are viewed as undesirable and have been removed ahead of the etherification processes. These undesirable light materials, in the case of $C_4$ olefin conversion to produce butyl ethers, will normally include hydrogen, methane, and ethane. In the case of $C_5$ olefin conversion in the production of aryl ethers, the undesirable materials can include $C_4$ hydrocarbons.

It is a broad object of this invention to improve the arrangement and operation of an etherification process that receives the dehydrogenating feed stream of dehydrogenated hydrocarbons.

A more specific object of this invention is to reduce the capital and utility cost associated with the separation and recycle of components from the effluents of the combined processes for dehydrogenating hydrocarbons and the production of ethers.

Another object of this invention is to simplify the separation facilities in a combined process for the dehydrogenation of dehydrogenatable hydrocarbons and the etherification of the dehydrogenated hydrocarbons.

BRIEF SUMMARY OF THE INVENTION

It has now been discovered that capital and operating costs associated with the etherification of dehydrogenation zone effluents having undesirable light end materials can be improved by a process that allows some of these materials to be passed through the etherification zone. Thus, in a broad aspect, this invention charges the liquid effluent from a dehydrogenation separator, that recovers hydrogen from the dehydrogenation zone effluent, to an etherification zone. The effluent entering the etherification zone will contain saturated and unsaturated $C_4$ or $C_5$ hydrocarbons including isoolefins and $C_3$ hydrocarbons. The etherification zone reacts essentially all of the isoolefins with a monohydroxy alcohol to produce an ether product and produce an etherification zone effluent that contains an ether product and is deficient in the reacted olefin. The etherification effluent is first separated to recover the ether product. That portion of the etherification zone effluent that contains hydrocarbons for the recycle to the dehydrogenation zone passes through a methanol recovery zone for the recovery of methanol and is further fractionated to remove $C_3$ and lighter hydrocarbons and produce a stream of saturate $C_4$ or $C_5$ hydrocarbons for recycle to the dehydrogenation zone. The stream of $C_3$ and lighter hydrocarbons will also contain essentially all of the light oxygenates from the etherification effluent that are not removed by the methanol recovery zone. In a typical etherification process, the hydrocarbon stream may contain 100 to 1000 wt. ppm of dimethylether, produced by the decomposition of methanol over the etherification catalyst.

Thus, in a broad embodiment, the present invention consists of a process for producing ethers. In the process, a dehydrogenation effluent containing isoolefins and isoalkanes having between four and five carbon atoms and hydrocarbons having less than four carbon atoms enters an etherification zone. Upon combination with a $C_1$-$C_5$ monohydroxy alcohol at etherification conditions and in the presence of an etherification catalyst, essentially all the isoolefins are converted to corresponding ethers. An etherification zone effluent containing unreacted isoalkanes, ether, alcohol, and $C_3$ and lighter hydrocarbons enters a first separation zone. The first separation zone produces an ether product stream and a separator stream containing isoalkanes, alcohol, and hydrocarbons having less than four carbon atoms. The separator stream passes through an alcohol recovery unit that removes alcohol for return to the etherification zone. The remainder of the separator stream enters another separation zone which divides the separator stream into a recycle stream that is composed primarily of $C_4$ or $C_5$ isoalkanes and a light gas stream containing the $C_3$ and lighter hydrocarbons along with other light oxygen containing compounds, such as dimethylether (DME).

In a more specific embodiment, this invention is a process for producing MTBE. Practice of this process includes combining a recycle stream and a feed stream to provide a dehydrogenation zone input stream containing isobutane and hydrogen. Contacting the input stream with a dehydrogenation catalyst at dehydrogenation conditions in the dehydrogenation zone yields a mixed stream of isobutane, isobutene and hydrogen which also contains $C_3$ and lighter hydrocarbons. The dehydrogenation zone effluent enters a hydrogen recovery section. After substantial depletion of hydrogen, the dehydrogenation zone effluent enters an etherification zone. Admixture with methanol and contact with an etherification catalyst at etherification conditions in the etherification zone effects an essentially complete conversion of isobutene into MTBE and produces an etherification zone effluent containing MTBE, isobutane, and $C_3$ and lighter hydrocarbons. A first separation zone receives the etherification zone effluent and separates it into an MTBE product stream and a separation stream containing methanol, isobutane, and $C_3$ and lighter hydrocarbons. A methanol recovery zone removes methanol from the separation stream and transfers the remainder of the stream to a second separation zone. The second separation zone separates the separation stream into an isobutane fraction that forms the recycle stream for the dehydrogenation zone and an off gas stream including $C_3$ and lighter hydrocarbons. Other oxygenates that may be present in the recycle stream and may interfere with the operation of the dehydrogenation zone such as dimethyl ether are also removed with the $C_3$ and lighter hydrocarbons.

Additional embodiments, aspects, and details of this invention are set forth in the following detailed description.

BRIEF DESCRIPTION OF THE DRAWING

The drawing schematically shows a combined dehydrogenation and etherification process. This process includes a dehydrogenation reactor section 10, a hydrogen recovery section 12, an MTBE reactor section 14, and an MTBE product separator 16, a methanol recovery unit 18, and a depropanizer 20.

DETAILED DESCRIPTION OF THE INVENTION

The operation of this invention uses the effluent from a dehydrogenation zone or reaction section for the production of olefins from dehydrogenatable hydrocarbons. Dehydrogenatable hydrocarbons for this invention include isoalkanes having 4 or 5 carbon atoms. A suitable feed of dehydrogenatable hydrocarbons will often contain light hydrocarbons (i.e., those having less carbon atoms than the primary feed components) which, for the purpose of this invention, serve as contaminants. In most cases, olefins are excluded from the dehydrogenation zone recycle in order to avoid the formation of dienes which produce unwanted by-products in many of the olefin conversion processes.

Along with the dehydrogenatable hydrocarbons, the feed to the dehydrogenation zone of the present invention comprises an $H_2$ rich stream, preferably containing at least 75 mole percent $H_2$ The presence of $H_2$ within the dehydrogenation zone serves several purposes. First, the $H_2$ acts to suppress the formation of hydrocarbonaceous deposits on the surface of the catalyst, more typically known as coke. Secondly, $H_2$ can act to suppress undesirable thermal cracking. Because $H_2$ is generated in the dehydrogenation reaction and comprises a portion of the effluent, the $H_2$ rich stream introduced into the reaction zone generally comprises recycle $H_2$ derived from separation of the dehydrogenation zone effluent. Alternately, the $H_2$ may be supplied from suitable sources other than the dehydrogenation zone effluent.

The dehydrogenatable hydrocarbon stream and $H_2$ stream are introduced into a dehydrogenation reaction zone. The dehydrogenation reaction zone of this invention preferably comprises at least one radial flow reactor through which the catalytic composite gravitates downwardly to allow a substantially continuous replacement of the catalyst with fresh and/or regenerated catalyst. A detailed description of the moving bed reactors herein contemplated may be obtained by reference to U.S. Pat. No. 3,978,150. The dehydrogenation reaction is a highly endothermic reaction which is typically effected at low (near atmospheric) pressure conditions. The precise dehydrogenation temperature and pressure employed in the dehydrogenation reaction zone will depend on a variety of factors such as the composition of the paraffinic hydrocarbon feedstock, the activity of the selected catalyst, and the hydrocarbon conversion rate. In general, dehydrogenation conditions include a pressure of from about 0 to about 35 bars and a temperature of from about 480° C. (900° F.) to about 760° C.

(1400° F.). A suitable hydrocarbon feedstock is charged to the reaction zone and contacted with the catalyst contained therein at a liquid hourly space velocity of from about 1 to about 10. Hydrogen, principally recycle hydrogen, is suitably admixed with the hydrocarbon feedstock in a mole ratio of from about 0.1 to about 10. Preferred dehydrogenation conditions, particularly with respect to $C_4$–$C_5$ paraffinic hydrocarbon feedstocks, include a pressure of from about 0 to about 5 bars and a temperature of from about 540° C. (1000° F.) to about 705° C. (1300° F.), a liquid hourly space velocity of from about 1 to about 5, and a hydrogen/hydrocarbon mole ratio of from about 0.5 to about 2.

The dehydrogenation zone of this invention may use any suitable dehydrogenation catalyst. Generally, the preferred catalyst comprises a platinum group component, an alkali metal component, and a porous inorganic carrier material. The catalyst may also contain promoter metals which advantageously improve the performance of the catalyst. It is preferable that the porous carrier material of the dehydrogenation catalyst be an absorptive high surface area support having a surface area of about 25 to about 500 $m^2/g$. The porous carrier material should be relatively refractory to the conditions utilized in the reaction zone and may be chosen from those carrier materials which have traditionally been utilized in dual function hydrocarbon conversion catalysts. A porous carrier material may, therefore, be chosen from an activated carbon, coke or charcoal, silica or silica gel, clays and silicates including those synthetically prepared and naturally occurring, which may or may not be acid-treated as, for example, attapulgus clay, diatomaceous earth, kieselguhr, bauxite; refractory inorganic oxides such as alumina, titanium dioxide, zirconium dioxides, magnesia, silica alumina, alumina boria, etc.; crystalline alumina silicates such as naturally occurring or synthetically prepared mordenite or a combination of one or more of these materials. The preferred porous carrier material is a refractory inorganic oxide, with the best results being obtained with an alumina carrier material. The aluminas, such as gamma alumina, give the best results in general. The preferred catalyst will have a gamma alumina carrier which is in the form of spherical particles having relatively small diameters on the order of about 1/16 inch.

The preferred dehydrogenation catalyst also contains a platinum group component. Of the platinum group metals, which include palladium, rhodium, ruthenium, osmium and iridium, the use of platinum is preferred. The platinum group component may exist within the final catalyst composite as a compound such as an oxide, sulfide, halide, oxysulfide, etc., or an elemental metal or in combination with one or more other ingredients of the catalyst. It is believed that the best results are obtained when substantially all the platinum group components exist in the elemental state. The platinum group component generally comprises from about 0.01 to about 2 wt. % of the final catalytic composite, calculated on an elemental basis. It is preferred that the platinum content of the catalyst be between about 0.1 and 1 wt. %. The preferred platinum group component is platinum, with palladium being the next preferred metal. The platinum group component may be incorporated into the catalyst composite in any suitable manner such as by coprecipitation or cogelation with the preferred carrier material, or by ion-exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the supportiwth an aqueous solution of chloroplatinum or chloropalladic acid. An acid such as hydrogen chloride is generally added to the impregnation solution to aid in the distribution of the platinum group component throughout the carrier material.

Additionally, the preferred catalyst contains an alkali metal component chosen from cesium, rubidium, potassium, sodium, and lithium. The preferred alkali metal is normally either potassium or lithium, depending on the feed hydrocarbon. The concentration of the alkali meta may range from about 0.1 to 5 wt. %, but is preferably between 1 and about 4 wt. % calculated on an elemental basis. This component may be added to the catalyst by the methods described above as a separate step or simultaneously with the solution of another component. With some alkali metals, it may be necessary to limit the halogen content to less than 0.5 wt. % and preferably less than 0.1 wt. %, while others may have higher halogen content.

As noted previously, the dehydrogenation catalyst may also contain promoter metal. One such preferred promoter metal is tin. The tin component should constitute about 0.01 to about 1 wt. % tin. It is preferred that the atomic ratio of tin to platinum be between 1:1 and about 6:1. The tin component may be incorporated into the catalytic composite in any suitable manner known to effectively disperse this component in a very uniform manner throughout the carrier material. Thus, the component may be added to the carrier by coprecipitation.

A preferred method of incorporating the tin component involves coprecipitation during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into an oil bath. The tin component may also be added through the utilization of a soluble decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

Operation of the dehydrogenation zone will produce a mixture of hydrogen and hydrocarbons. Normally, a portion of the hydrocarbons will include an equilibrium mixture of the desired isoolefin and its isoalkane precursor. Additional hydrocarbons having fewer carbon atoms than the desired isoolefin also form part of the effluent, originate as impurities in the feed or are produced by sidereactions in the dehydrogenation zone. These additional hydrocarbons will usually comprise methane, ethane, ethylene, propylene and propane. Where the dehydrogenation effluent goes to an etherification process for the reaction of $C_5$ isoolefins to produce ethers, such as tertiary amyl ether (TAME) $C_4$ hydrocarbons may be part of the additional hydrocarbons which enter the etherification zone.

Effluent from the dehydrogenation reaction section passes to a hydrogen recovery section. This separation section removes hydrogen from the efluent and recovers it in high purity for recycle to the dehydrogenation reaction section. Separation steps for the removal of hydrogen will normally include cooling and compressing with subsequent cooling and flashing in a separation vessel. Such methods for the separation pf hydrogen and light gases are well known by those skilled in the art. The advantages of this invention can be realized by operating the hydrogen recovery section to allow essentially all $C_3$ and higher hydrocarbons to pass through the olefin conversion zone. At minimum, these steps will remove primarily hydrogen and methane from the dehydrogenation zone effluent. These separation facilities are preferably designed to reduce the concentration of hydrogen and methane in the effluent with minimum loss of $C_4+$. Reduction of hydrogen and methane will, as explained later in more detail, allow the etherification zone to operate without an excessive increase in pressure over that required for operation of etherification process with a more complete removal of light end materials.

In other embodiments these facilities can be designed to remove substantial quantities of $C_1$ and $C_2$ hydrocarbons in addition to hydrogen. To the extent that liquid phase conditions are desired in the etherification zone, removal of these light gases will permit reduction of the etherification zone operating pressure. The advantages associated with the removal of additional $C_2$ hydrocarbons must be balanced against the loss of additional product hydrocarbons such as $C_4$ and higher hydrocarbons. After removal of at least hydrogen, methane, and some ethane/ethylene the remaining light hydrocarbons and undehydrogenated hydrocarbons are passed with the olefins to an etherification zone.

In the etherification zone, olefins are combined with one or more monohydroxy alcohols to obtain an ether compound having a higher boiling point than the olefin precursor. In order to obtain complete conversion, an excess of the alcohol is usually present in the etherification zone. It has been found that the presence of hydrocarbons having fewer carbon atoms than the olefin reactants will not unduly interfere with the operation of the etherification zone. The major changes in the etherification zone resulting from the presence of the additional light materials such as methane, ethane, ethylene, etc. will be an increased pressure and additional throughput. It has also been discovered that these changes will be relatively small and will not interfere with the olefin reactions or increase the operational utilities, particularly, when substantial methane is removed with hydrogen. Another characteristic of most etherification processes that contributes to the advantages of this invention is that they can convert essentially all of the isoolefins having a particular range of carbon numbers to a higher boiling ether.

A preferred etherification process is one for the production of MTBE. Converting essentially all of the isobutene to MTBE eliminates the need for separating that olefin from isobutane. As a result, downstream separation facilities are simplified and operated more economically since these facilities need to handle a reduced volume of closely boiling materials. Several suitable etherification processes have been described in the available literature, with these processes being presently used to produce MTBE. The preferred form of the etherification zone is similar to that described in U.S. Pat. No. 4,219,678 and shown in the previously cited paper. In this instance, the isobutene or other isoolefin, methanol or other feed alcohol, and a recycle stream containing recovered excess alcohol are passed into the etherification zone and contacted with an acidic catalyst while maintained at etherification conditions.

A wide range of materials are known to be effective as etherification catalysts for the preferred reactants including mineral acids such as sulfuric acid, boron trifluoride, phosphoric acid on kieselguhr, phosphorus-modified zeolites, heteropoly acids, and various sulfonated resins. The use of a sulfonated solid resin catalyst is preferred. These resin type catalysts include the reaction products of phenolformaldehyde resins and sulfuric acid and sulfonated polystyrene resins including those crosslinked with divinylbenzene. Further information on suitable etherification catalysts may be obtained by reference to U.S. Pat. Nos. 2,480,940, 2,922,822, and 4,270,929 and the previously cited etherification references.

A wide range of operating conditions are employed in processes for producing ethers from olefins and alcohols. Many of these include vapor, liquid or mixed phase operations. Processes operating with vapor or mixed phase conditions may be suitably employed in this invention. The preferred etherification process uses liquid phase conditions.

The range of etherification conditions for processes operating in liquid phase still includes a broad range of suitable conditions including a superatmospheric pressure sufficient to maintain the reactants as a liquid phase, generally below about 50 bars, and a temperature between about 30° C. (85° F.) and about 100° C. (210° F.). Even in the presence of additional light materials, pressures in the range of 10 to 40 bars are sufficient. A preferred temperature range is from 50° C. (120° F.) to 100° C. (210° F.). The reaction rate is normally faster at higher temperatures but conversion is more complete at lower temperatures. High conversion in a moderate volume reaction zone can, therefore, be obtained if the initial section of the reaction zone, e.g., the first two-thirds, is maintained above 70° C. (160° F.) and the remainder of the reaction zone is maintained below 50° C. (120° F.). This may be accomplished most easily with two reactors. The ratio of feed alcohol to isoolefin should normally be maintained in the broad range of 1:1 to 2:1. With the preferred reactants, good results are achieved if the ratio of methanol to isobutene is between 1.05:1 and 1.5:1. An excess of methanol, above that required to achieve satisfactory conversion at good selectivity, should be avoided as some decomposition of methanol to dimethylether may occur which may increase the load on separation facilities.

The effluent from the etherification zone includes at least product ethers, $C_3-$ hydrocarbons, dehydrogenatable hydrocarbons, and any excess alcohol. The effluent may also include $C_1-C_2$ hydrocarbons, small amounts of hydrogen that were dissolved with the feed components, and small amounts of other oxygen containing compounds that were formed in the etherification zone such as dimethyl ether. The effluent from the etherification zone passes from the etherification zone to a separation section for the recovery of product.

Thus, the first separation section is to separate the ether product from the effluent of the etherification zone. The product ethers are typically withdrawn as a bottoms stream from a fractionation column. The initial separation between the ether products and the remainder of the etherification zone effluent will be performed in a single column. Depending upon the specification for the ether product, it may be suitable for use as withdrawn from the bottom of the separation column or may require additional separation to remove methanol which may be present in the form of an azeotrope mixture of the product ether. The column will also provide at least one additional separator stream made up of a lighter fraction that contains reactants for the dehydrogenation zone such as isoalkane and alcohol reactants for use in the etherification zone which make up in part the remainder of the etherification zone effluent. Alcohol present in the separator stream is unreacted excess alcohol in an amount equivalent to its azeotropic composition with the hydrocarbons. Any alcohol, in excess of the amount taken as an azeotrope with the separator stream, will leave the separator with the ether product and may be recovered by additional fractionation steps as previously described. The cutccontaining the reactants will also contain $C_3$ hydrocarbons and in most cases will include $C_1$-$C_2$ hydrocarbons and some hydrogen. The separation section can be arranged to further separate hydrogen and $C_1$-$C_2$ hydrocarbons from the cut containing the reactants. This can be done, for example, in a reflux system on the top of the distillation column that condenses the heavier components of the reactant cut for liquid recycle to the column and venting of the lighter hydrogen and hydrocarbon gases. In the preferred embodiment of this invention, a reactant stream deficient only in the etherification product is recovered from the etherification separation section.

The reactant cut from the etherification separation section enters a methanol recovery. unit. The methanol recovery unit extracts methanol from the reactant cut. The methanol recovery unit can use any methanol recovery technique that effect a substantially a complete recovery of methanol and reduces its concentration in the reactant cut to approximately less than 10 wt. ppm. The preferred alcohol recovery system will be a water washed system that absorbs alcohol from the remaining hydrocarbons in the reactant stream and includes a separation column for recovery of the methanol and recycle of the water. Another type of methanol recovery unit will use a solid adsorbent to preferentially adsorb the alcohol component from the reactant cut. Alcohol separated in the methanol recovery unit is preferably recycled to the etherification zone to provide a portion of the methanol reactant. The remainder of the reactant cut enters another separation section. This second section divides the reaction cut into a recycle stream made up of isoalkanes that will be recycled to the dehydrogenation zone and a lighter fraction having a lower boiling point then the recycled isoalkanes. Where the etherification zone produces MTBE, the second separation zone will function as a depropanizer and recover an isobutane bottoms stream for recycle to the dehydrogenation zone. A relatively lighter hydrocarbon stream made up of $C_3$ and lighter hydrocarbons is recovered overhead. In most cases, the separation zone can be designed as a single column with the recycle stream recovered as a bottoms streams and the lighter hydrocarbons taken overhead. The separator can also be operated to remove the unwanted oxygen-containing compounds that may be formed as by-products in the etherification zone. One such compound that can be removed overhead by the second separator is dimethyl ether which has a lower boiling than propane. Where a water-wash system is used for the methanol recovery unit, the separator can also be operated to remove entrained as well as soluble water from the dehydrogenatable hydrocarbons.

When separaing the isoalkanes or dehydrogenatable hydrocarbons the separation facilities normally need not provide a good cut between the light ends and the dehydrogenatable hydrocarbons. Since the dehydrogenation zone can normally tolerate these light hydrocarbons, allowing some light hydrocarbons to pass with dehydrogenatable hydrocarbons eases the severity of the separation zone.

This invention will be further described in the context of an example for the production of MTBE. The description of this invention in terms of this specific process example is not meant to limit this invention to the particular details disclosed herein. This example is based on engineering calculations and experience with the operation of similar process units. The Figure provides a schematic drawing for this type of operation. The drawing shows only the equipment that is useful in the description of the process. The utilization of other miscellaneous hardware such as heaters, coolers, valves, reboilers, pumps, instrumentation, and controls have been omitted as not essential to a clear understanding of the process, the use of such hardware being well within the purview of one skilled in the art.

Referring then to the drawing, a hydrocarbon input stream comprising isobutane is charged to line 21 from a deisobutanizer column which is not shown. The feed stream is combined with a hereinafter described recycle isobutane stream 22 to obtain a dehydrogenation feed stream 23 which passes through a dehydrogenation separation section 12. In separation section 12, the dehydrogenation feed stream is heat exchanged and transported to dehydrogenation reactor section 10 by way of line 24 at a temperature of about 40° C. (100° F.) and at a pressure of about 3 bars (40 psig). A hydrogen-rich recycle stream from line 26 provides hydrogen to dehydrogenation section 10. The recycle hydrogen rate is set to provide a desired hydrogen/hydrocarbon ratio. Within dehydrogenation section 10, hydrogen is mixed with the feed stream and the combined stream is further heat exchanged with the effluent from the dehydrogenation reactor effluent. After heat exchange, the combined stream is further heated to the desired reaction temperature before entering the reactors in zone 10.

Preferably, dehydrogenation reactor section 10 comprises multiple stacked or side by side reaction zones, and a combined stream of hydrogen and hydrocarbon feed is processed serially through said zones each of which contains a particulate catalyst disposed as an annular-form bed movable downwardly through said zones. The combined stream is then processed through said annular-form beds in a substantially radial flow and, since the dehydrogenation reaction is endothermic in nature, intermediate heating of the reactant stream between zones is the preferred practice. The moving catalyst bed permits a continuous addition of fresh and/or regenerated catalyst and the withdrawal of spent catalyst. The moving bed system herein contemplated s illustrated in U.S. Pat. No. 3,647,680 in conjunction with a continuous catalyst regeneration system, and in U.S. Pat. No. 3,978,150 with reference to the dehydrogenation of paraffinic hydrocarbons.

Regardless of the actual reactor details, the hot effluent stream is heat exchanged with the combined feed as previously described and recovered from the dehydrogenation section 10 through line 28. The composition of the effluent taken by line 28 is given in the Table. The reactor section effluent stream, at a temperature of about 95° C. (200° F.) and a pressure slightly above atmospheric is passed to dehydrogenation separation section 12. In separation section 12, the dehydrogenation effluent is cooled and compressed, and again cooled to obtain a dried reactor effluent vapor phase stream for further cooling and condensing where it is exchanged against feed stream 23 and finally introduced into one or more separators. The separators yield a liquid hydrocarbon phase and a hydrogen-rich vapor phase which, after heat exchange, exits separation section 12 at a temperature of about 40° C. (100° F.) and a pressure of about 50 psig. A portion of the hydrogen-rich vapor phase, substantially equivalent to the net hydrogen product, is taken from separation section 12 through line 30 and processed for further use. The remainder of the hydrogen-rich vapor stream continues through line 26 and enters dehydrogenation reactor section 10 as previously described. The liquid hydrocarbon phase is pumped from separation section 12 through line 32 at a pressure of about 10 to 20 bars and at a temperature of about 65° C. (150° F.). The contents of line 32 have the relative composition given in the Table.

TABLE

| | Compositions in mol % | | | | | | |
|---|---|---|---|---|---|---|---|
| | Line 28 | Line 32 | Line 38 | Line 42 | Line 52 | Line 54 | Line 22 |
| $H_2$ | 53.0 | Trace | Trace | — | TR | TR | — |
| $C_1$ | 8.6 | 2 | 2 | — | 3.5 | 30.3 | — |
| $C_2$ | 0.6 | 1 | 1 | — | 1.73 | 15.2 | — |
| $C_3$ | 2.0 | 4 | 4 | — | 7.0 | 52.3 | 1.1 |
| isobutane | 18.5 | 48 | 47.5 | <0.5 | 82.6 | 1.8 | 93.0 |
| isobutene | 16.5 | 43 | 1 | <0.5 | 1.73 | — | 2.0 |
| Other $C_4$'s | 0.8 | 2 | 2 | <0.5 | 3.5 | — | 3.9 |
| $C_5$ and heavier hydrocarbons | — | — | — | — | — | — | — |
| MEOH | — | — | 1 | TR | TR | — | — |
| MTBE | — | — | 41.5 | 99.0 | — | — | — |
| DME and Other Oxygenates | — | — | — | .5 | 0.05 | 0.4 | TR |
| | 100 | 100 | 100 | 100 | 100 | 100 | 100 |

The contents of line 32 enter MTBE reaction section 14 to which methanol is added via line 34 to provide a 1:1 to 1.1:1 ratio of methanol to isobutylene. The added methanol consists of fresh methanol and recycle methanol added via line 36. The combined reactants pass through a sulfonic resin catalyst at temperature of 65° C. (150° F.) and a pressure of 10 to 15 bars (150 to 200 psig). An etherification zone effluent is withdrawn by line 38 and has the composition given in the Table. Line 38 carries the etherification zone effluent to etherification separation section 16 at a temperature of 45°-70° C. and a pressure of 5 to 15 bars.

The etherification separation section 16 includes an ordinary tray-type column 40 of conventional design that receives the contents of line 38 at a tray elevation located at or below the column midpoint and divides the etherification zone effluent into three fractions. An MTBE product fraction at a purity of 99 plus % leaves the bottom of the column through line 42 and its composition is given in the Table. The remainder of the etherification zone effluent, withdrawn overhead via line 44, is cooled in exchanger 46 to a temperature of 40° C. and split between reflux which line 48 returns to the column and a net overhead withdrawn via line 50.

Methanol recovery section 18 receives the net overhead from line 50. The methanol recovery unit consists of a water wash system that extracts essentially all of the methanol. The amount of methanol withdrawn depends on the azeotropic composition at the overhead operating conditions. Line 36 returns the extracted methanol to the etherification zone in a mannrr previously described. Passage through section 18 reduces the concentration of methanol in the net overhead stream to less than 10 wt. ppm.

Line 52 carries the net overhead stream, which has the composition given in the Table, at a temperature of 40° C. and a pressure of 15-25 bars to depropanizer 20. Depropanizer column 20 is a fractionation column of ordinary construction. Column 20 splits the contents of line 52 into a bottoms stream and a net overhead stream. Line 22 carries the bottoms stream back to the dehydrogenation zone as the previously described recycle. The net overhead is withdrawn by line 54 and has the composition given in the Table.

The Example shows that a high yield of MTBE product at relatively high purity can be obtained by. the method of this invention. The flow requires only two simple separation facilities to obtain the MTBE product, an isobutane recycle and the removal of light materials following the etherification of the hydrogen deficient dehydrogenation zone recycle. In addition, the use of the depropanizer as a means of removing the water and oxygen-containing compounds allows the process to operate with only a methanol recovery unit and does not require an additional recovering unit for other oxygen containing compounds.

What is claimed is:

1. A process for producing ethers comprising:
   (a) passing the effluent from a dehydrogenation zone to an etherification zone, the deydrogenation zone effluent comprising isoolefins and isoalkanes having four or five carbon atoms and includng $C_3$ hyrdocarbons and hydrocarbons having less than three carbon atoms;
   (b) combining the dehydrogenation zone effluent with a $C_1$-$C_5$ monohydroxy alcohol in said etherification zone at etherification conditions to obtain essentially complete conversion of said isoolefins and an etherifidation zone effluent comprising isoalkanes, alcohol, ether and $C_3$ and lignrer hydrocarbons;
   (c) passing said etherification zone effluent to a first separation zone and recovering at least a first stream comprising an ether product and a second stream comprising isoalkanes, alcohol and including $C_3$ hydrocarbons and hydrocarbons having less than three carbon atoms;
   (d) recovering alcohol from said second stream in an alcohol recovery zone and returning at least a portion of the recovered alcohol to said etherification zone;
   (e) passing said second stream from said alcohol recovery zone to a second separation zone to separate isoalkanes from said second stream and obtain a recycle stream consisting essentially of isoalkanes; and,
   (f) recycling said recycle stream to said dehydrogenation zone.

2. The process of claim 1 wherein said dehydrogenation zone effluent stream includes $C_4$ isoolefins, said monohydroxy alcohol of step (b) is methanol, and said etherification zone produces MTBE.

3. The process of claim 1 wherein said dehydrogenation zone effluent stream includes $C_1$-$C_3$, hydrocarbons and traces of hydrogen.

4. The process of claim 1 wherein said etherification zone contains a sulfonated solid resin catalys and operates at a temperature in the range of from 30°-100° C. (85°-210° F.) and a pressure of from 10-40 bars.

5. The process of claim 1 wherein said methanol recovery zone comprises a water wash system.

6. The process of claim 1 wherein said first separation zone separates said etherification zone effluent into a bottoms stream comprising said first stream and an overhead stream comprising said second stream.

7. A process for producing MTBE comrpising:
 (a) combinina a recycle stream and a feed stream to provide a dehydrogenation zone input stream, said feed stream comprising isobutane and hydrogen;
 (b) contacting said input stream with a dehydrogenation catalyst at dehydrogenation conditions in a dehydrogenation zone to obtain a first effluent stream comprising isobutene, isobutane, hydrogen, and including $C_3$ hydrocarbons and light hydrocarbons having less than three carbon atoms;
 (c) passing at least a portion of said first effluent stream into a hydrogen recovery section to remove hydrogen from said first effluent;
 (d) passing said first effluent from said hydrogen recovery section to an etherification zone, combining said first effluent with methanol, and contacting said first effluent stream in said etherification zone with an etherification catalyst at etherification conditions to react essentially all of said isobutene and obtain a second effluent stream comprising isobutane, MTBE, methanol, oxygenate compounds other than methanol, and including hydrocarbons having less than four carbon atoms;
 (e) separating said second effluent in a first separation zone into a product stream comprising an MTBE product stream and a separator stream comprising isobutane, methanol, oxygenate compounds other than methanol, and including hydrocarbons having less than four carbon atoms per molecule;
 (f) passing said separator stream to a methanol recovering zone and recovering essentially all of the methanol from said separator stream in siad methanol recovery zone;
 (g) returning at least a portion of the methanol from said recovery zone to said etherification zone;
 (h) passing said separator stream to a second separation zone and separating isobutane from said separator stream; and
 (i) recycling the isobutane separated in said second separation zone to said dehydrogenation zone as said recycle stream.

8. The process of claim 7 wherein said dehydrogenation zone conditions include a temperature in the range of 500°-700° C. (930°-1290° F.) and a pressure of from 0.2 to 2 bars.

9. The process of claim 7 wherein said etherification conditions include a temperature in the range of 30°-100° C. (85°-210° F.) and a pressure of 10 to 20 bars.

10. The process of claim 9 wherein said dehydrogenation catalyst comprises platinum on alumina and said etherification catalyst is a sulfonic acid resin.

11. The process of claim 7 wherein essentailly all of said oxygenate compounds are recovered in an overhead stream from said second separation zone.

12. The process of claim 11 wherein said oxygen containing compounds include dimethylether and oxygen.

13. The process of claim 7 wherein said first effluent stream includes $C_2$ and $C_3$ hydrocarbons.

* * * * *

UNITED STATES PATENT AND TRADEMARK OFFICE
CERTIFICATE OF CORRECTION

PATENT NO. : 4,806,695
DATED : February 21, 1989
INVENTOR(S) : Vora et al.

It is certified that error appears in the above-identified patent and that said Letters Patent is hereby corrected as shown below:

In Column 12, line 45: Change "lignrer" to --lighter--.

Signed and Sealed this

Twenty-fifth Day of July, 1989

Attest:

DONALD J. QUIGG

Attesting Officer

Commissioner of Patents and Trademarks